United States Patent
Yamada

(10) Patent No.: US 6,878,956 B2
(45) Date of Patent: Apr. 12, 2005

(54) APPARATUS AND METHOD FOR INSPECTING A SURFACE OF AN INSPECTION OBJECT

(76) Inventor: Yoshiro Yamada, 2-5-13, Kakinokizaka, Meguro-ku, Tokyo 152-0022 (JP)

(*) Notice: Subject to any disclaimer, the term of this patent is extended or adjusted under 35 U.S.C. 154(b) by 0 days.

(21) Appl. No.: 10/383,830

(22) Filed: Mar. 7, 2003

(65) Prior Publication Data
US 2003/0151008 A1 Aug. 14, 2003

Related U.S. Application Data

(63) Continuation of application No. PCT/JP02/06856, filed on Jul. 5, 2002.

(30) Foreign Application Priority Data

Jul. 9, 2001 (JP) .......................................... 2001-207321
Jul. 13, 2001 (JP) .......................................... 2001-214340

(51) Int. Cl.⁷ ............................................. G01N 21/88
(52) U.S. Cl. ................................................. 250/559.45
(58) Field of Search ....................... 250/559.45–559.48, 250/208.1; 382/258, 141

(56) References Cited

U.S. PATENT DOCUMENTS 5,230,027 A * 7/1993 Kikuchi ...................... 382/147

FOREIGN PATENT DOCUMENTS

| JP | 9-304286 | 11/1997 |
| JP | 2001-4552 | 1/2001 |
| JP | 2001-10024 | 1/2001 |
| JP | 2001-143079 | 5/2001 |

* cited by examiner

Primary Examiner—Thanh X. Luu
(74) Attorney, Agent, or Firm—Ohlandt, Greeley, Ruggiero & Perle, L.L.P.

(57) ABSTRACT

A surface inspection apparatus inputs image data obtained by scanning an inspection object by a camera which includes a line image sensor into calculation means. The surface inspection apparatus comprises a line memory and adder to add image data of two adjacent main scanning lines to generate an image data string, adds the image data in a block including a plurality of pixels continuous in a main scanning direction by the calculation processor to generate added data in the block, calculates a correlated value of the added data in the blocks adjacent to each other in the main scanning direction, and judges the correlated value with a threshold value by judgment means to obtain a surface state of the inspection object.

12 Claims, 8 Drawing Sheets

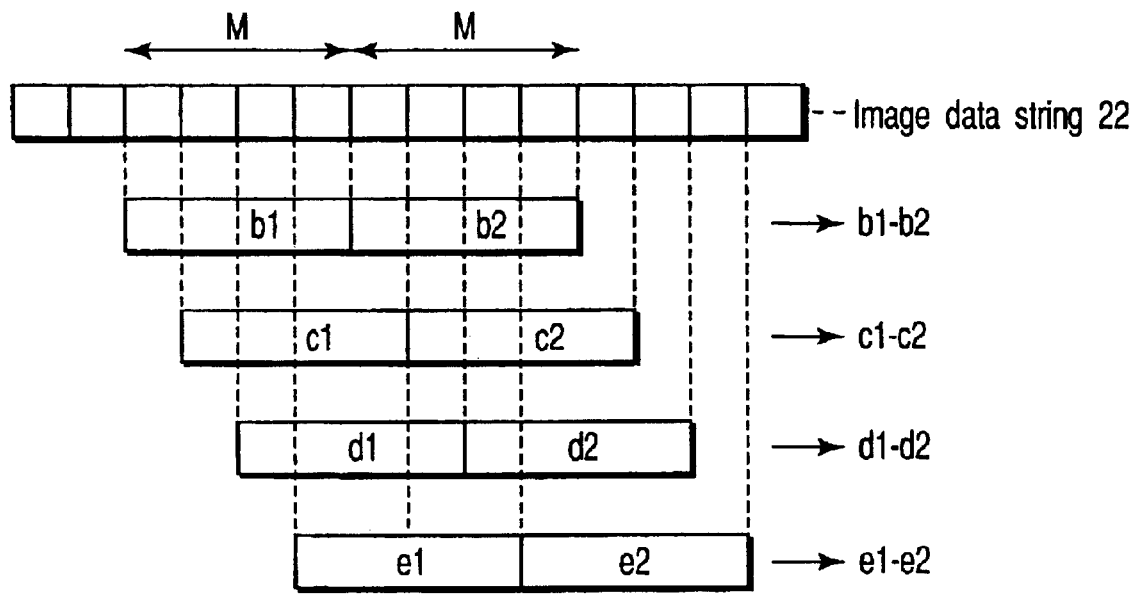
F I G. 4
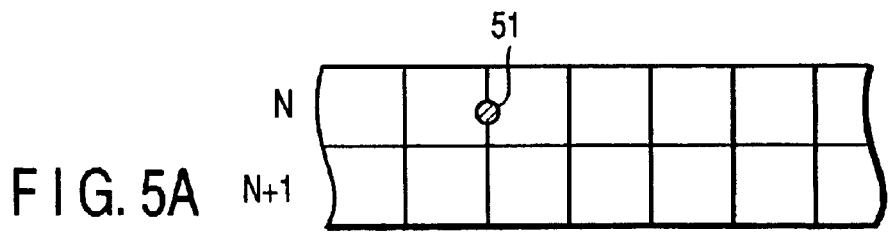
F I G. 5A
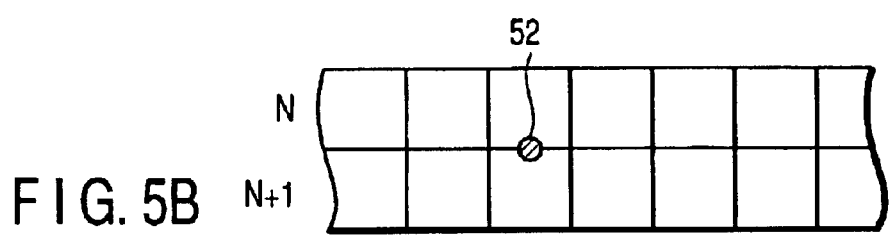
F I G. 5B
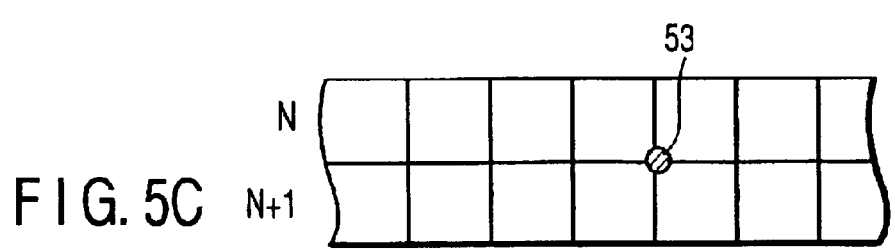
F I G. 5C

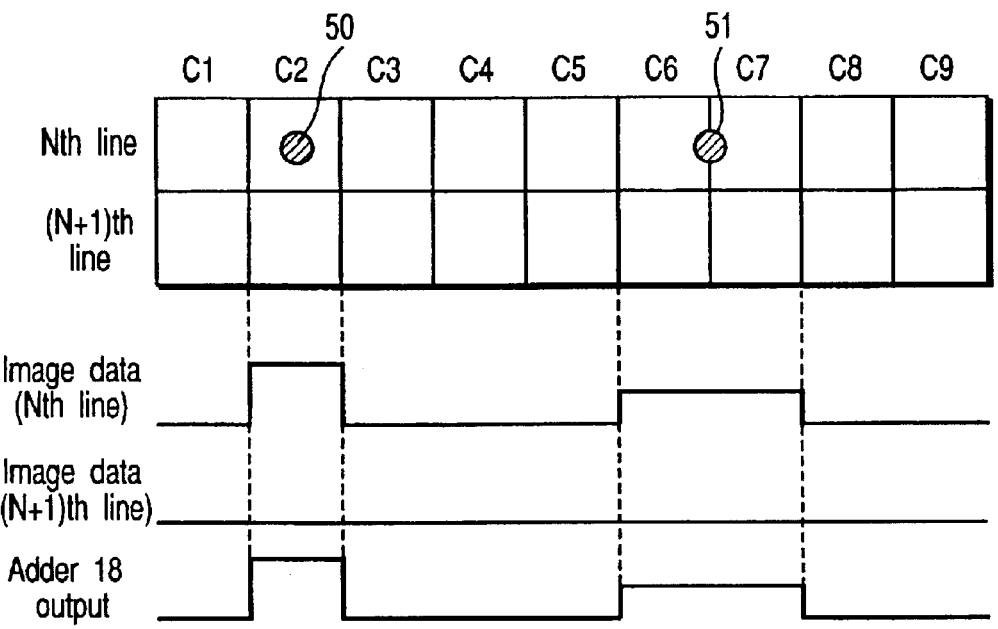
F I G. 6A
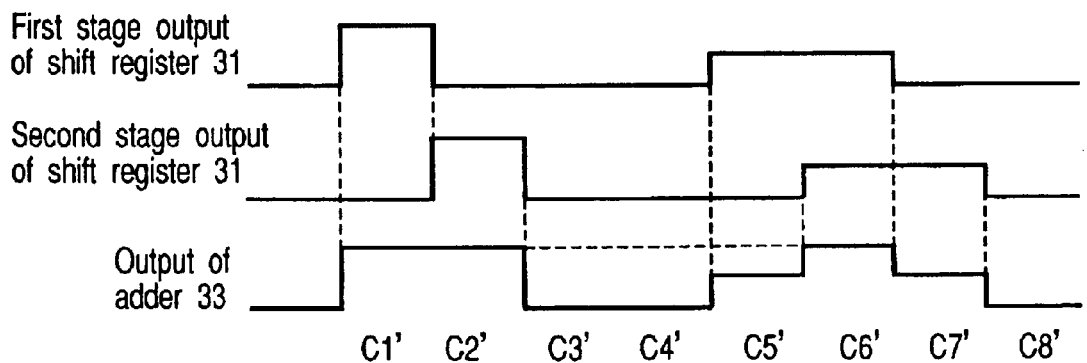
F I G. 6B

APPARATUS AND METHOD FOR INSPECTING A SURFACE OF AN INSPECTION OBJECT

CROSS-REFERENCE TO RELATED APPLICATIONS

This is a Continuation Application of PCT Application No. PCT/JP02/06856, filed Jul. 5, 2002, which was not published under PCT Article 21(2) in English.

This application is based upon and claims the benefit of priority from the prior Japanese Patent Applications No. 2001-207321, filed Jul. 9, 2001; and No. 2001-214340, filed Jul. 13, 2001, the entire contents of both of which are incorporated herein by reference.

BACKGROUND OF THE INVENTION

1. Field of the Invention

The present invention relates to a surface inspection apparatus and method in which a camera including an image sensor is used to perform a surface inspection of defects, including damage, dirt and the like of various inspection objects, such as molded articles.

2. Description of the Related Art

In a related art, for example, in inspecting surface defects of inspection objects such as pressed articles, drawn articles, and rolled articles, cameras such as a CCD camera have previously been used. The CCD camera includes a line image sensor constituted by one-dimensionally arranging photoelectric conversion devices (line image sensor). The camera one-dimensionally scans the inspection object, and image data obtained in this manner is subjected to calculation processing and inspected.

In a two-dimensional image sensor for use in video cameras, in general, there are only several hundred image pickup pixels in a view field width direction. On the other hand, in a line image sensor, it is possible to integrate several thousand image pickup pixels in the view field width direction. Therefore, a line image sensor can perform surface inspection of broad inspection objects such as steel, paper, and film, which is impossible with a two-dimensional image sensor.

In the image sensor of the photoelectric conversion device of this type of camera, there is a variation in reading precision. This variation is caused by a difference in sensitivity of each photoelectric conversion device constituting the image sensor, and is referred to as a device dispersion, and this value is generally about 3%. In the above-described related-art surface inspection apparatus, unless there is a brightness change exceeding the device dispersion, fine defects cannot be detected. It is said that a visual light/shade detection precision is in a range of 1/1500 to 1/2000, therefore a surface inspection apparatus using the line image sensor has a precision of only 1/60 of that of visual inspection, and it has been assumed to be impossible to replace visual inspections.

Therefore, various methods of compensating for the device dispersion of the image sensor have been considered. One example of a technique is known comprising: adding image data of a block including a plurality of pixels which are continuous in a main scanning direction in an image data string obtained by the line image sensor; and performing correlation calculation of added data of adjacent blocks.

However, a defect extending over the pixels adjacent to each other on one main scanning line can be detected in this method, but it is impossible to detect a defect extending over adjacent main scanning lines, and a defect extending over the pixels adjacent to each other on the main scanning line and also extending over the adjacent main scanning lines. Therefore, there has been a limitation in improvement of the inspecting precision.

BRIEF SUMMARY OF THE INVENTION

An object of the present invention is to provide a surface inspection apparatus and method in which it is possible to detect defects on an inspection object, such as a defect extending over adjacent main scanning lines or a defect extending over pixels adjacent to each other on the main scanning line and also extending over the adjacent main scanning lines, and in which a surface state can be inspected with good precision.

According to the present invention, there is provided a surface inspection apparatus comprising:

a camera comprising a line sensor which scans an inspection object in a main scanning direction to obtain image data;

sub-scanning means for moving the camera and inspection object with respect to each other in a sub-scanning direction crossing at right angles to the main scanning direction; and calculation means for subjecting the image data output from the camera to calculation processing to inspect a surface state of the inspection object, the calculation means comprising: image data string generation means for adding the image data of two main scanning lines adjacent to each other in the sub-scanning direction to generate an image data string; and judgment means for using the image data string to inspect the surface state of the inspection object.

Additional objects and advantages of the present invention will be set forth in the description which follows, and in part will be obvious from the description, or may be learned by practice of the present invention.

The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention and, together with the general description given above and the detailed description of the embodiments given below, serve to explain the principles of the present invention in which:

FIG. 4 is an explanatory view of an operation of the calculation processor shown in FIG. 3;

FIGS. 5A, 5B and 5C are explanatory views of various defects on an inspection object;

FIGS. 6A and 6B are diagrams showing a relation of the defect which exists only in one main scanning line and the corresponding image data and added data in a block;

DETAILED DESCRIPTION OF THE INVENTION

Embodiments of the present invention will be described hereinafter with reference to the drawings.

First Embodiment

Figure 1:
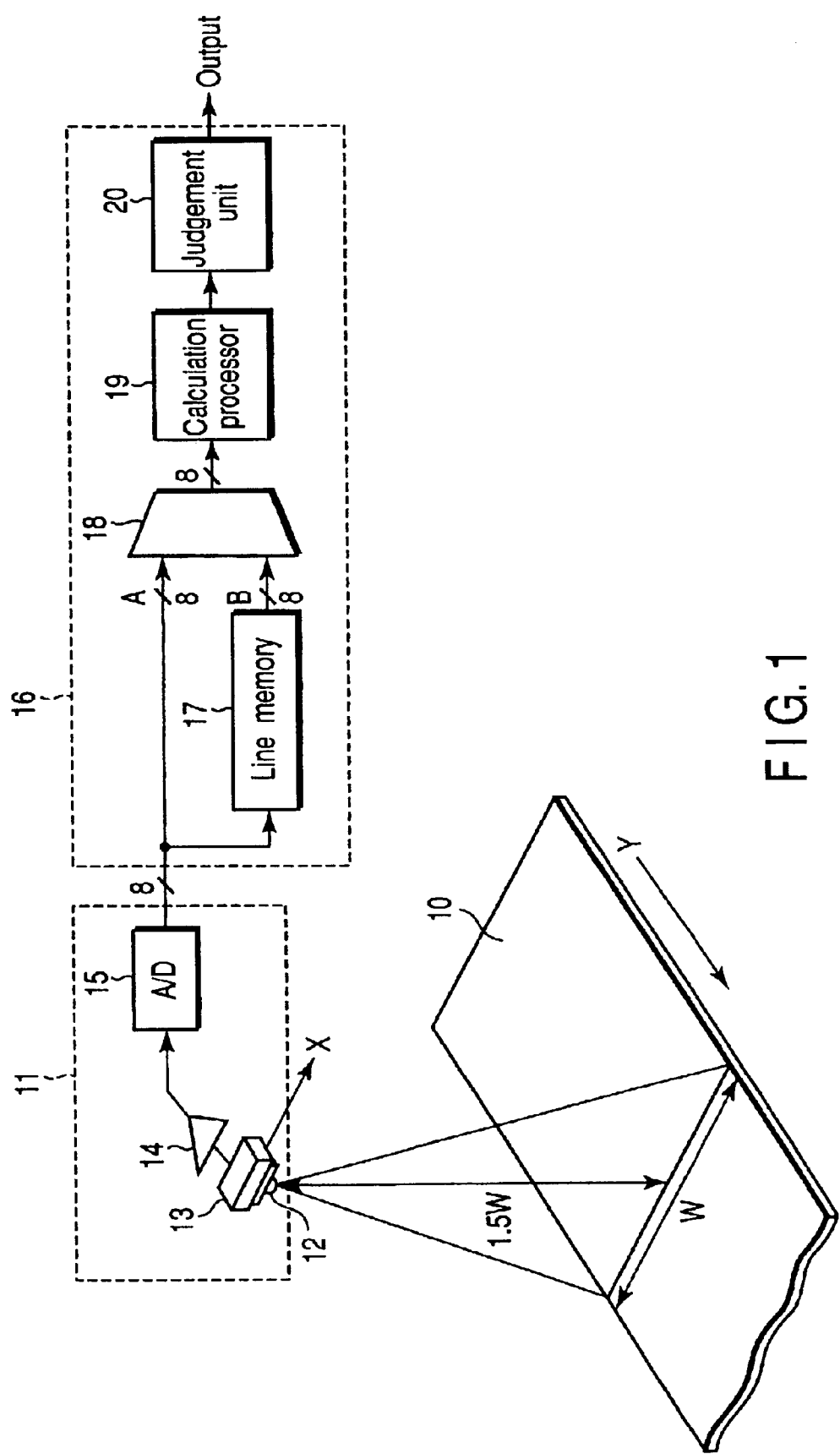
FIG. 1 is a block diagram showing a constitution of a surface inspection apparatus according to a first embodiment of the present invention.

FIG. 1 is a diagram showing a constitution of a surface inspection apparatus according to a first embodiment of the present invention. Examples of an inspection object 10 include a pressed article, drawn article, and rolled article, and the object moves in a direction shown by an arrow Y (sub-scanning direction) by a main scanning apparatus (not shown) at a surface inspection time. It is to be noted that to inspect the molded article at a molding time, a conveyance mechanism of a molding machine functions as a sub-scanning apparatus, and the sub-scanning apparatus does not have to be especially disposed. A digital camera 11 is disposed opposite to the inspection object 10.

The digital camera 11 comprises an objective lens 12, line image sensor 13 such as a CCD line image sensor, amplifier 14, and A/D converter 15. An image on the surface of the inspection object 10 is focused on the line image sensor 13 via the objective lens 12. When a reading width on the inspection object 10 by the line image sensor 13 is assumed to be W, and the objective lens 12 is a standard lens, a distance (objective distance) to the inspection object 10 from the camera 11 is set to about 1.5 W.

The line image sensor 13 is constituted by arranging a plurality of (e.g., 5120) photoelectric conversion devices in a direction shown by an arrow X (main scanning direction). A sub-scanning apparatus (not shown) scans the inspection object 10 which relatively moves in a direction (sub-scanning direction) crossing at right angles to the main scanning direction to read a surface state of the inspection object 10, and outputs an image signal.

The sub-scanning apparatus moves the image sensor 13 and the image of the inspection object 10 formed on the image sensor 13 with respect to each other in the sub-scanning direction crossing at right angles to the main scanning direction. The sub-scanning apparatus includes a function (a) which moves the inspection object 10 with respect to the line image sensor 13 in the sub-scanning direction. The sub-scanning apparatus may further include a function: (b) which moves the line image sensor 13 with respect to the inspection object 10 in the sub-scanning direction; (c) which moves the objective lens 12 with respect to the line image sensor 13 in the sub-scanning direction; or (d) which moves the line image sensor 13 and objective lens 12 with respect to the inspection object 10 in the sub-scanning direction.

Here, especially in (b), (c), (d), the line image sensor 13 or objective lens 12 may be moved (vibrated) using micro actuators in which micro driving is possible, such as a laminated piezoelectric actuator and electrostatic actuator.

The image signal output from the line image sensor 13 is amplified by the amplifier 14, further converted, for example, to eight-bits parallel digital data by the A/D converter 15, and output as image data from the digital camera 11.

The image data output from the digital camera 11 is input into an image processing apparatus 16. The image processing apparatus 16 subjects the input image data to predetermined image processing to output an inspection result of a surface state of the inspection object 10, and comprises a line memory 17, adder 18, calculation processor 19, and judgment unit 20 in this example.

The line memory 17 is a memory in which the image data for at least one main scanning line input from the digital camera 11 is stored, and comprises the same number of stages of shift registers or first-in and first-out (FIFO) memories as that of photoelectric conversion devices (e.g., 5120 devices) in the line image sensor 13.

The image data output from the digital camera 11 is supplied to a first input terminal of the adder 18, and also supplied to the line memory 17. An output of the line memory 17 is supplied to a second input terminal of the adder 18. The adder 17 adds image data A, B of input/output of the line memory 17.

Figure 2:
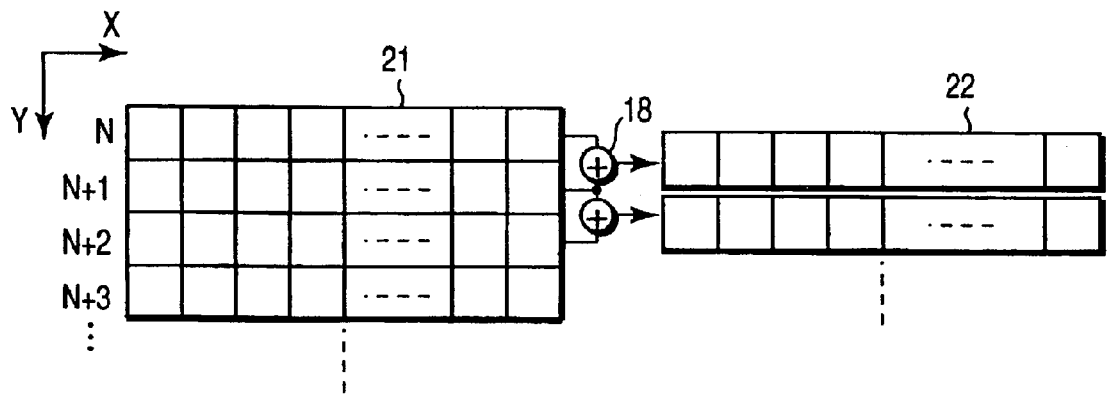
FIG. 2 is an explanatory view of an operation for adding image data of two main scanning lines adjacent to each other in a sub-scanning direction to generate an image data string in the first embodiment.

Here, the image data input into first and second input terminals A, B of the adder 18 correspond to the image signal obtained from the same device of the line image sensor 13. That is, the input terminal B delays by time for one main scanning line with respect to the input terminal A of the adder 18 by the line memory 17. For example, when the image data corresponding to the i-th (i=1, 2, . . . ) device of the line image sensor 13 is input into the input terminal A, the image data obtained before by one main scanning line corresponding to the same i-th device is input into the input terminal B from the line memory 17. Therefore, as shown in FIG. 2, the adder 18 adds image data 21 of two main scanning lines input into the input terminals A, B and disposed adjacent to each other in a sub-scanning direction (N-th and (N+1)-th lines, (N+1)-th and (N+2)-th lines, . . . ) to generate an image data string 22.

The image data string 22 generated by an image data string generator formed of the line memory 17 and adder 18 in this manner is input into the calculation processor 19. The calculation processor 19 adds (accumulates) the image data of a block including a plurality of pixels continuous in a main scanning direction X to the image data string from the adder 18 to generate in-block added data, and uses the data as pixel data of a first pixel in the block. The processor 19 also repeats processing to calculate a correlated value of added data in the blocks adjacent to each other in the main scanning direction while shifting the position of the block in the main scanning direction.

Figure 3:
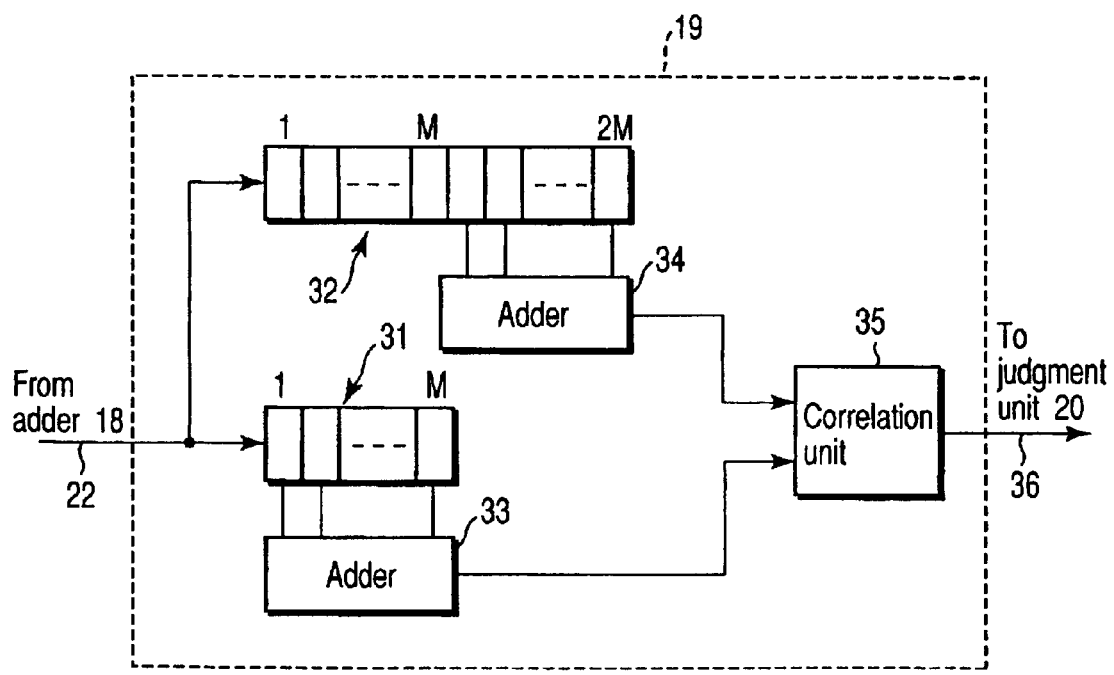
FIG. 3 is a block diagram showing a constitution of a calculation processor in the first embodiment.

Concretely, as shown in FIG. 3, the calculation processor 19 comprises M stages of a shift register 31 and 2M stages of a shift register 32 connected so that the image data string 22 (see FIG. 2) from the adder 18 is input into the first stages thereof; an adder 33 which adds the outputs of the respective stages of the shift register 31; an adder 34 which adds the outputs of the rear M stages of the shift register 32; and a correlation unit 35 to which the outputs of the adders 33 and

34 are supplied. Here, when the pixels of the image data of one main scanning line are divided into blocks including a plurality of pixels continuous in the main scanning direction, M denotes the number of pixels constituting one block. The value of M can preferably be arbitrarily changed, and is, for example, in a range of 1 to 111.

FIG. 4 is an explanatory view of an operation of the calculation processor 19. In the adder 33, for the image data string 22 output from the adder 18, the image data of one block including M pixels continuous in the main scanning direction is added. The adder 34 adds the image data of the next block adjacent to the block to which the image data is added by the adder 33 in the main scanning direction in the image data string 22. Here, assuming that in-block added data output from the adders 33 and 34 are b1 and b2, for example, a difference b1-b2 between the both data is obtained as a correlated value 36 in the correlation unit 35.

Every time the data of the new pixel of the image data string 22 is input into the shift registers 31 and 32, as shown in FIG. 4, the position of the block to which the image data is added by the adders 33 and 34 is successively shifted in the main scanning direction, and a similar operation is performed. By such an operation, the adders 33 and 34 successively output in-block added data c1 and c2; d1 and d2; e1 and e2; . . . , and the correlation unit 35 successively obtains c1-c2, d1-d2, e1-e2 which are the correlated values 36.

Here, the correlation unit 25 obtains the difference between the adjacent in-block added data as the correlated value 36, but may also obtain a ratio (b1/b2, . . . ) of the adjacent in-block added data as the correlated value 36. The correlated value 36 output from the correlation unit 25 is input into the judgment unit 20 in FIG. 1. The judgment unit 20 is formed, for example, of a comparator, and it compares the correlated value 36 output from the correlation unit 26 with an appropriate threshold value to judge presence/absence of a surface defect of the inspection object 10, and outputs a judged result which is an inspection result of the surface state.

That is, when there is a defect on the inspection object 10, the magnitude of the image data corresponding to the same device of the line image sensor 13 changes with time during sub-scanning, that is, relative movement of the inspection object 10 in the vicinity of the defect. Thereby, since the correlated value 36 obtained by the correlation unit 35 increases and exceeds the threshold value in the judgment unit 20, the judgment unit 20 can recognize this defect. The judged result of the judgment unit 20 is processed, for example, by a personal computer and displayed in a display apparatus (not shown).

According to the surface inspection apparatus of the present embodiment constituted as described above, by an accumulation function by performing the addition in the block in the calculation processor 19, and self correlation function by establishing correlation between the in-block added data adjacent to each other in the main scanning direction, the influence of the device dispersion of the line image sensor 13 is removed. Moreover, the correlated value 36 obtained by the correlation unit 35 increases, and detection sensitivity of the defect can be enhanced.

Furthermore, according to the present embodiment, especially the line memory 17 and adder 18 are used to add the image data of two main scanning lines adjacent to each other in the sub-scanning direction, and the image data string obtained in this manner is input into the calculation processor 19. Thereby, when a defect 51 on the inspection object 10 exists only in one main scanning line (N-th line in the drawing) as shown in FIG. 5A, detection is of course possible. Additionally, a defect 52 extending over two adjacent main scanning lines (N-th and (N+1)-th lines in the drawing) as shown in FIG. 5B, and a defect 53 extending over the pixels adjacent to each other on the main scanning line and also extending over two adjacent main scanning lines as shown in FIG. 5C can also be detected, and high-precision inspection is further possible.

This principle will be described hereinafter in detail.

First, when the defect 51 on the inspection object 10 exists only in one main scanning line as shown in FIG. 5A, as compared with the image data (camera 11 output) corresponding to a defect 50 existing in one pixel as shown in FIG. 6A, the output of the image data corresponding to the defect 51 existing over two pixels is reduced. Since the data of one pixel is distributed to two pixels, an output level is halved. Since there is not any defect in the next line, the output is 0, and the output (image data string 22) of the adder 18 for adding the image data of two lines adjacent to each other in the sub-scanning direction is the same as the image signal of the N-th line. For the image data string 22, the pixel data in the block of the main scanning direction is accumulated by the accumulation function of the calculation processor 19 to form predetermined pixel data, for example, of the first pixel in the block. Here, for the sake of convenience of description, assuming that the block includes two pixels, as shown in FIG. 6B, the adder 33 adds two image data strings which deviate from each other by one pixel. Therefore, since the next pixel data is added to each pixel data, and the level of the image data of a pixel c6' corresponding to the defect 51 is the same as that of the image data of a pixel c2' corresponding to the defect 50 (the level increases), not only the defect 50 but also the defect 51 can easily be detected.

Figure 7A:
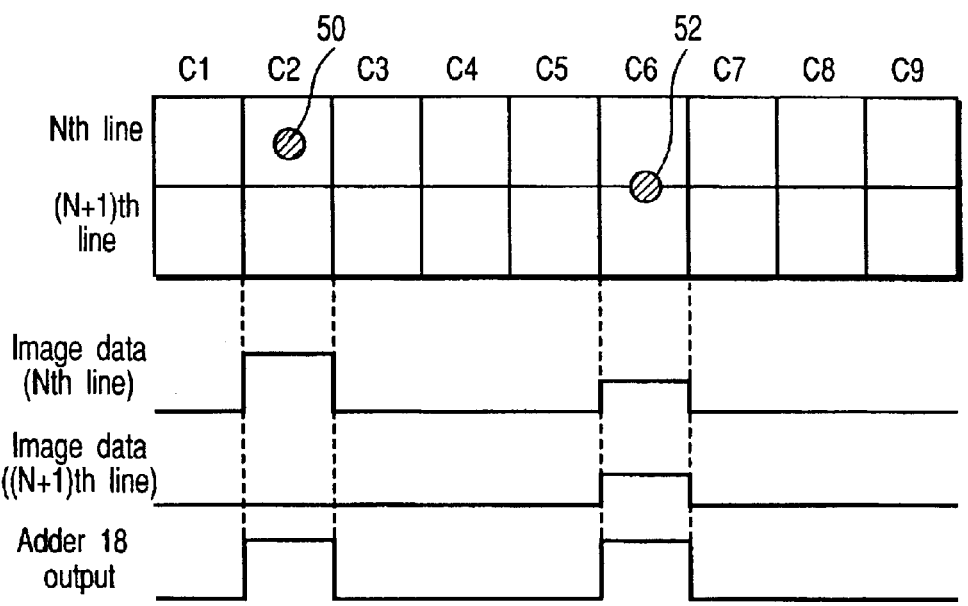
FIGS. 7A and 7B are diagrams showing a relation of the defect which exists over two adjacent main scanning lines and the corresponding added data in the block.

Next, when there is a defect 52 extending over two adjacent main scanning lines, as shown in FIG. 5B, as compared with the image data corresponding to the defect 50 existing in one pixel in one main scanning line as shown in FIG. 7A, the output of the image data corresponding to the defect 52 is reduced. This also applies to N-th and (N+1)-th lines. However, by the adder 18 which adds the image data of two lines adjacent to each other in the sub-scanning direction, the output of the image data string 22 corresponding to the defect 52 is the same as that of the image data string 22 corresponding to the defect 51. Therefore, even the defect 52 which exists over two main scanning lines can easily be detected.

Figure 7B:
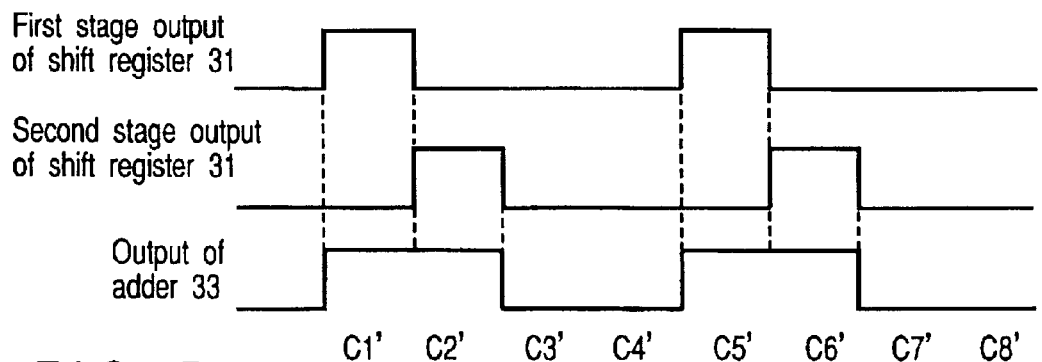
Figure 8A:
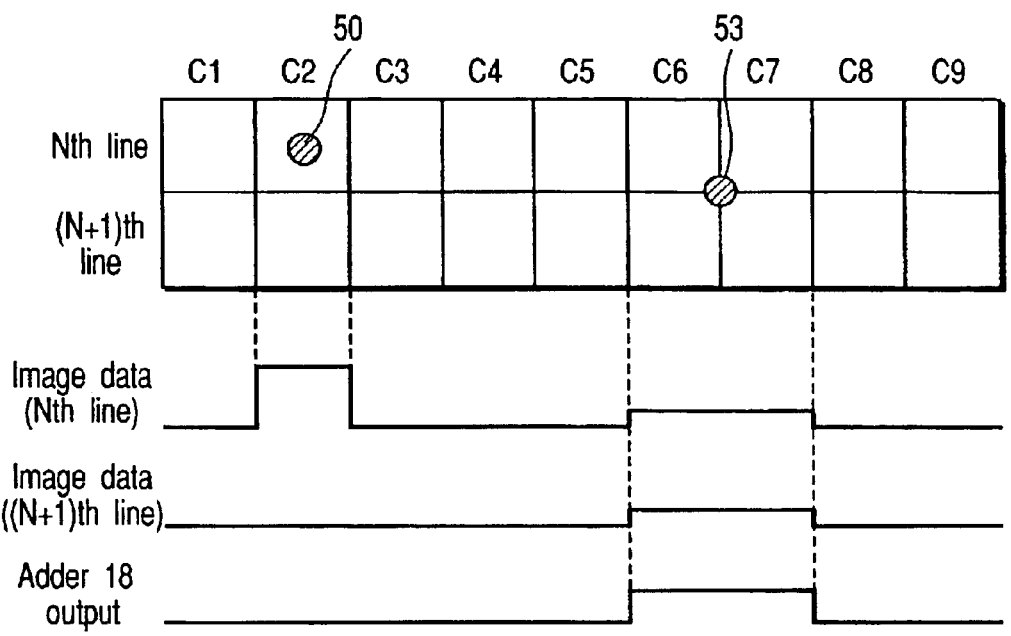
FIGS. 8A and 8B are diagrams showing a relation of the defect which extends over pixels adjacent to each other on the main scanning line and also extends over two adjacent main scanning lines and the corresponding image data and the added data in the block.
Figure 8B:
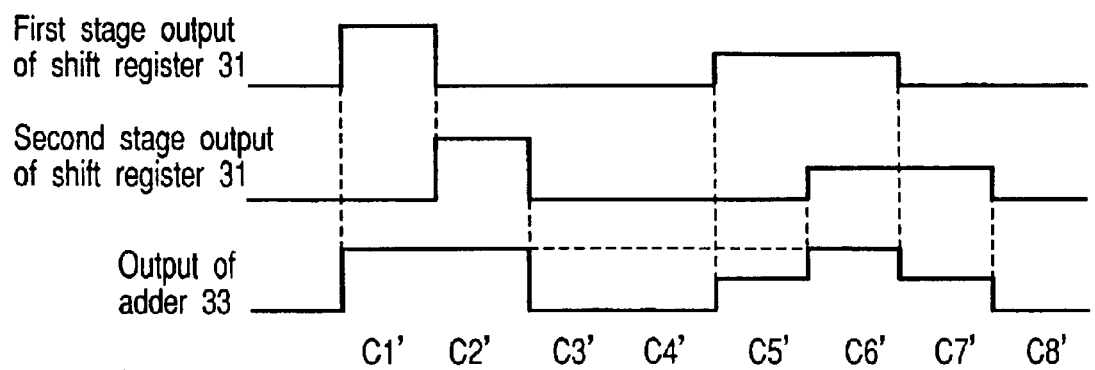

It is to be noted that FIG. 7B shows the in-block added data. However, in this example, since there is no defect extending over two pixels in the main scanning direction, the addition in the block is unnecessary. Furthermore, when there is a defect 53 extending over the pixels adjacent to each other on the main scanning line and also extending over two adjacent sub scanning lines, as shown in FIG. 5C, as compared with the image data corresponding to the defect 50 existing in one pixel in one main scanning line as shown in FIG. 8A, the output of the image data corresponding to the defect 53 is reduced. The data of one pixel is distributed into four pixels, and therefore both the N-th and (N+1)-th lines have an output level which is ¼ of that of the image data corresponding to the defect 53. However, by the adder 18 which adds the image data of two lines adjacent to each other in the sub-scanning direction, the output level of the image data string 22 corresponding to the defect 53 is amplified to ½. The image data string 22 is used as the predetermined pixel data, for example, of the first pixel in the block by an effect by the accumulation function of the calculation processor 19 in the main scanning direction. Here, for the sake of convenience of description, assuming that the block includes two pixels, the adder 33 adds two image data strings deviating from each other by one pixel as shown in FIG. 8B. Therefore, since the next pixel data is added to each pixel data, and the level of the image data of the pixel c6' corresponding to the defect 53 is the same as that of the image data of the pixel c2' corresponding to the defect 50 (the level increases), not only the defect 50 but also the defect 53 can easily be detected.

Second Embodiment

Next, a second embodiment of the present invention will be described with reference to FIG. 9. The constitution of the surface inspection apparatus according to the second embodiment is the same as that of the first embodiment shown in FIG. 1.

In the first embodiment, when the line memory 17 and adder 18 are used to add the image data of two main scanning lines adjacent to each other in the sub-scanning direction Y to the image data 21 output from the digital camera 11 and to generate the image data string 22, the image data of two pixels (pixels having the same position in the main scanning direction) adjacent to each other in the sub-scanning direction Y of these two main scanning lines are added.

Figure 9:
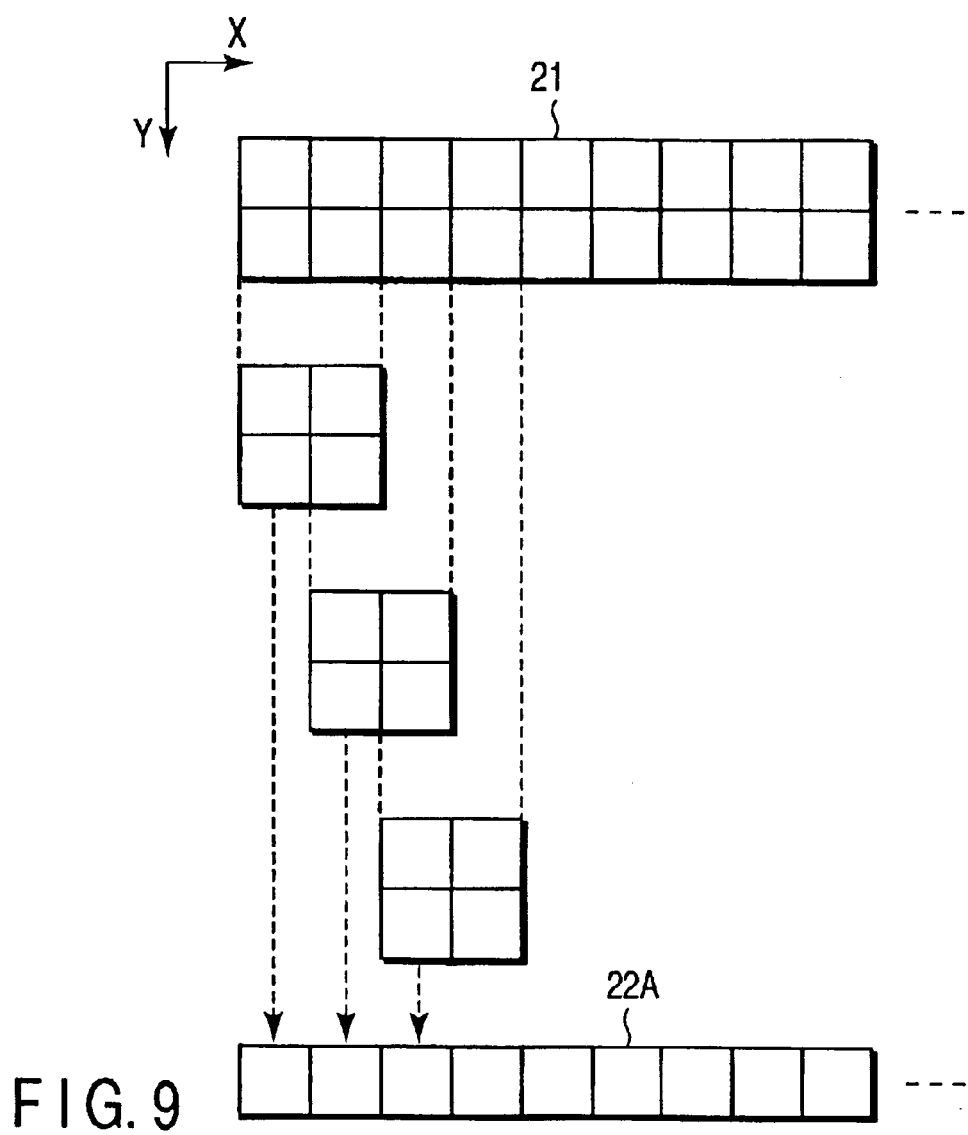
FIG. 9 is an explanatory view showing an operation for adding the image data of two main scanning lines adjacent to each other in a sub-scanning direction to generate the image data string in a second embodiment of the present invention.

However, the method of adding the image data of two main scanning lines adjacent to each other in the sub-scanning direction to generate the image data string is not limited to this, and the image data string may also be generated, for example, in a method shown in FIG. 9. This method comprises executing processing of adding the image data of four pixels adjacent to each other in the sub-scanning direction and main scanning direction to the image data 21 of two main scanning lines adjacent to each other in the sub-scanning direction Y while shifting the positions of the four pixels by the unit of one pixel in the main scanning direction, so that an image data string 22A is generated.

According to this method, since the magnitude of each piece of data of the image data string 22A is enlarged, inspecting precision can further be enhanced. Moreover, this is especially effective in detecting a defect 53 which exists over the pixels adjacent to each other on the main scanning line and over the adjacent main scanning lines as described, for example, with reference to FIGS. 5C and 8.

Third Embodiment

The whole constitution of the surface inspection apparatus according to the third embodiment is the same as that of the first embodiment shown in FIG. 1. In the same manner as in the second embodiment, a third embodiment also relates to modification of the generation method of the image data string.

Figure 10A:
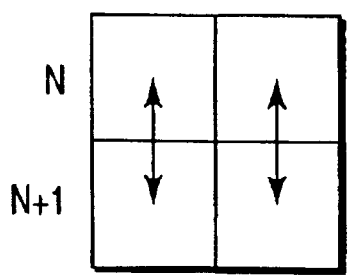
FIGS. 10A, 10B and 10C are explanatory views showing a modification example for adding the image data of two main scanning lines adjacent to each other in the sub-scanning direction to generate the image data string in a third embodiment.
Figure 10B:
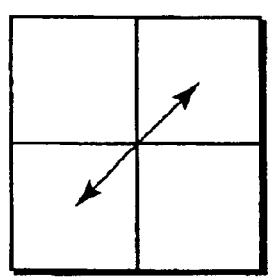
Figure 10C:
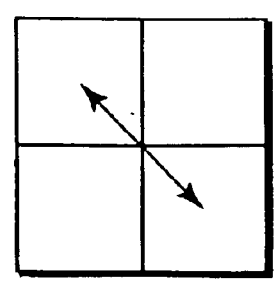

In the third embodiment, when the image data of two main scanning lines adjacent to each other in the sub-scanning direction is added to generate the image data string, in the same manner as in the first embodiment, as shown in FIG. 10A, the image data of two pixels (pixels having the same position in the main scanning direction) adjacent to each other in the sub-scanning direction of two main scanning lines is added to generate the image data string. In addition to this processing, processing of FIGS. 10B and 10C is also executed. FIG. 10B shows processing of adding the image data of the pixels adjacent to each other in an oblique right-ascending direction (first direction) with respect to the sub-scanning direction to generate the image data string. FIG. 10C shows processing of adding the image data of the pixels adjacent to each other in an oblique left-ascending direction (second direction) with respect to the sub-scanning direction to generate the image data string.

Figure 11:
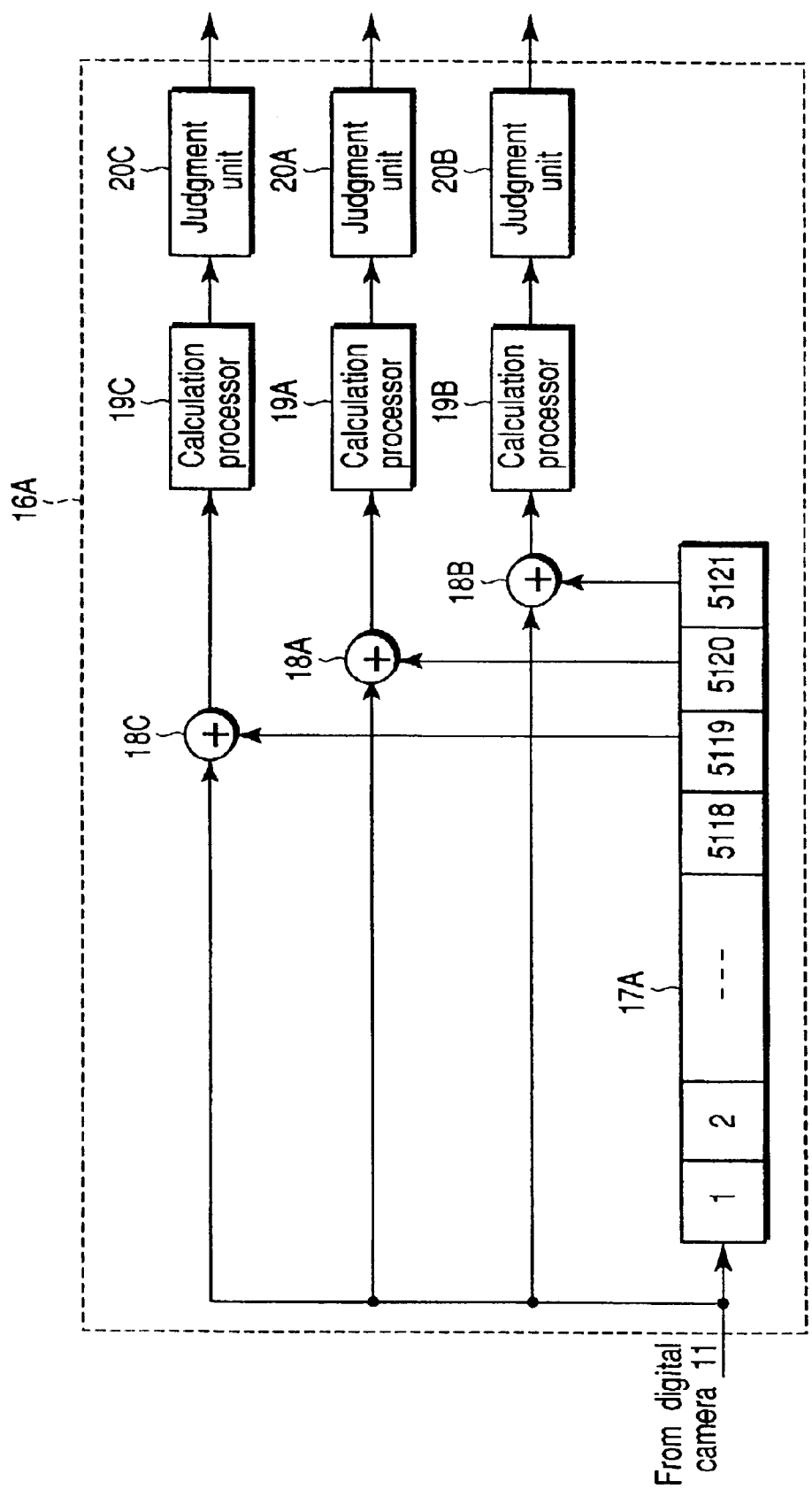
FIG. 11 is a block diagram showing a constitution of an image processing apparatus in the third embodiment.

FIG. 11 is a diagram showing a constitution of an image processing apparatus 16A in the third embodiment. A line memory 17A comprises the shift register including the number of pixels (5120 pixels in this example) for one main scanning line+1=5121 stages. The input of the shift register, output of the 5120-th stage, output of the 5121st stage, and output of the 5119-th stage are added by adders 18A, 18B and 18C, respectively. Thereby, the adder 18A outputs the image data string obtained by adding the image data of two pixels adjacent to each other in the sub-scanning direction of two main scanning lines shown in FIG. 10A. The adder 18B outputs the image data string obtained by adding the image data of the pixels adjacent to each other in the oblique right-ascending direction with respect to the sub-scanning direction shown in FIG. 10B. The adder 18C outputs the image data string obtained by adding the image data of the pixels adjacent to each other in the oblique left-ascending direction with respect to the sub-scanning direction as shown in FIG. 10C.

These image data strings are input into judgment units 20A, 20B and 20C via calculation processors 19A, 19B and 19C in the same manner as in the first embodiment, and judges with the threshold value. The judgment results of these judgment units 20A, 20B and 20C are processed, for example, by a personal computer and displayed on the display apparatus (not shown). They may be displayed in different colors, so that they can be distinguished from one another.

According to the present embodiment, for example, it is possible to easily detect even a very thin linear defect which exists on the inspection object 10 and which obliquely crosses the line image sensor 13. That is, such a defect appears over the pixels adjacent to each other in the oblique direction with respect to the sub-scanning direction on two main scanning lines as shown in FIG. 10B or 10C. Therefore, the image data of these pixels are added and subsequently processed by the calculation processor, and can easily be detected.

Additionally, the present invention can be variously modified and carried out. For example, the use of a line image sensor has been described in the above embodiments, but the present invention is also effective with the use of a two-dimensional image sensor (also referred to as an area sensor) in which the photoelectric conversion devices are arranged in a matrix form.

The pixels (photoelectric conversion devices) are arranged without any gap in the line image sensor, whereas a dead region for wiring exists lengthwise and breadthwise between the pixels in the two-dimensional image sensor. However, according to the present invention, a drop of detection sensitivity by such a dead region can be compensated for by an addition function of the image data of two main scanning lines adjacent to each other in the sub-scanning direction and accumulation function in the main scanning direction.

Moreover, in the embodiments, the line memory and adder are used to add the image data string obtained by adding the image data of two main scanning lines adjacent to each other in the sub-scanning direction in the block via the calculation processor, and subsequently the string is input into the judgment unit, but may also be input into the judgment unit without being passed through the calculation processor. Even in this constitution, an object of the present invention can be achieved.

Human eyeballs perform micro vibration called fixation micromotion. That is, it is supposed that eyeballs perform fixation micromotion separately from the motion in seeing in vertical and horizontal directions so as to prevent the retina from insensible for stimulation, and precision is increased. The main motion component of the fixation micromotion is the vertical direction.

In the present invention, the processing of addition of the image data of two adjacent main scanning lines corresponds to this fixation micromotion of human eyeballs. That is, in the present invention, the movement (micromotion) of the sub-scanning direction is performed by electronic or mechanical processes, and the image data string obtained by adding the image data of two adjacent main scanning lines is processed to perform surface inspection, so that inspecting precision is raised.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein. For example, the present invention can be practiced as a computer readable recording medium in which a program for allowing the computer to function as predetermined means, allowing the computer to realize a predetermined function, or allowing the computer to conduct predetermined means.

As described above, according to the present invention, defects, including those extending over main scanning lines on an inspection object or over pixels adjacent to each other on the main scanning line and extending to the adjacent main scanning line, can be detected, and a surface state can be inspected with good precision.

What is claimed is:

1. A surface inspection apparatus comprising:
    a camera comprising a line sensor for scanning an inspection object in a main scanning direction to obtain image data and scanning the inspection object in a sub-scanning direction crossing at right angles to the main scanning direction; and
    calculation means for subjecting image data output from the camera to calculation processing to inspect a surface state of the inspection object, wherein the calculation means comprises:
        image data string generation means for adding image data of two main scanning lines adjacent to each other in the sub-scanning direction to generate an image data string; and
        judgment means for using the image data string to inspect the surface state of the inspection object, wherein the judgment means comprises accumulation means for adding the image data in a block including a plurality of pixels continuous in the main scanning direction to the image data string to calculate added data in the block;
        correlation means for calculating a correlated value of the in-block added data of the blocks adjacent to each other in the main scanning direction; and
        means for judging the correlated value with a threshold value.

2. The surface inspection apparatus according to claim 1, wherein the image data string generation means adds image data of pixels in the same position in the main scanning direction to the image data of two main scanning lines adjacent to each other in the sub-scanning direction.

3. The surface inspection apparatus according to claim 2, wherein the image data string generation means adds image data of a first two pixels in a first main scanning line and adjacent to one another in the sub-scanning direction and a second two pixels in a second main scanning line adjacent to the first main scanning line and adjacent to each other in the sub-scanning direction to generate the image data.

4. The surface inspection apparatus according to claim 1, wherein the image data string generation means comprises:
    a line memory in which the image data output from the camera for at least one main scanning line is stored; and
    an adder for adding the image data of an input/output of the line memory to obtain the image data string.

5. The surface inspection apparatus according to claim 1, wherein the image data string generation means adds image data of a first two pixels in a first main scanning line and adjacent to one another in the sub-scanning direction and a second two pixels in a second main scanning line adjacent to the first main scanning line and adjacent to each other in the sub-scanning direction to generate a first image data string, adds image data of a third two pixels adjacent to each other in a first direction which is oblique with respect to the sub-scanning direction in the image data of two main scanning lines adjacent to each other in the sub-scanning direction to generate a second image data string, and adds the image data of a fourth two pixels adjacent to each other in a second direction which is oblique with respect to the sub-scanning direction in the image data of two main scanning lines adjacent to each other in the sub-scanning direction to generate a third image data string.

6. The surface inspection apparatus according to claim 5, wherein the image data string generation means comprises:
    a line memory in which the image data output from the camera for at least one main scanning line is stored;
    a first adder for adding the image data of an input of the line memory and certain image data preceding the input of the line memory by one main scanning line;
    a second adder for adding the image data of the input of the line memory and image data preceding the certain image data by one pixel; and
    a third adder for adding the image data of the input of the line memory and image data succeeding the certain image by one pixel.

7. The surface inspection apparatus according to claim 1, wherein the judgment means shifts the block in the main scanning direction by each pixel to repeat the in-block addition and correlation calculation.

8. The surface inspection apparatus according to claim 1, wherein the inspection object is moved in the sub-scanning direction with respect to the camera.

9. The surface inspection apparatus according to claim 1, wherein the camera is moved in the sub-scanning direction with respect to the inspection object.

10. The surface inspection apparatus according to claim 1, wherein the camera has a lens that is moved in the sub-scanning direction with respect to the line sensor.

11. The surface inspection apparatus according to claim 1, wherein the camera has a lens and image sensor that are moved in the sub-scanning direction with respect to the inspection object.

12. A surface inspection method using a camera comprising a line sensor for scanning an inspection object in a main scanning direction to obtain image data, the method comprising:

a step of moving the camera and inspection object with respect to each other in a sub-scanning direction crossing at right angles to the main scanning direction;

a step of adding the image data of two main scanning lines adjacent to each other in the sub-scanning direction in the image data output from the camera to generate an image data string; and a step of inspecting by using the image data string to inspect a surface state of the inspection object, wherein the inspection step comprises:

an accumulation step of adding the image data in a block including a plurality of pixels continuous in the main scanning direction in the image data string to calculate added data in the block;

a correlation step of calculating a correlated value of the in-block added data of the blocks adjacent to each other in the main scanning direction; and a step of judging the correlated value with a threshold value.

* * * * *